(12) United States Patent
Howard

(10) Patent No.: US 6,323,229 B1
(45) Date of Patent: Nov. 27, 2001

(54) N-ACYL AND N-AROYL ARALKYLAMIDES

(75) Inventor: Harry R. Howard, Bristol, CT (US)

(73) Assignee: Pfizer INC, New York, NY (US)

( * ) Notice: Subject to any disclaimer, the term of this patent is extended or adjusted under 35 U.S.C. 154(b) by 0 days.

(21) Appl. No.: 09/291,454

(22) Filed: Apr. 14, 1999

Related U.S. Application Data

(60) Provisional application No. 60/081,970, filed on Apr. 16, 1998.

(51) Int. Cl.⁷ .................. A61K 31/496; C07D 401/12; C07D 403/12; C07D 409/12; C07D 413/12
(52) U.S. Cl. .............. 514/373; 514/253.13; 514/254.02; 514/254.09; 514/255.03; 514/249; 514/300; 544/365; 544/367; 544/373; 544/379; 544/393; 544/165; 544/349; 544/354; 113/121; 113/133; 113/233; 113/234; 548/453; 548/557; 548/566; 548/570; 564/185
(58) Field of Search .................... 544/393, 365, 544/367, 373, 379; 514/252.13, 254.02, 254.09, 255.03, 253.13

(56) References Cited

FOREIGN PATENT DOCUMENTS

| 0810220 | 12/1997 | (EP) . |
| WO9734883 | 9/1997 | (WO) . |
| WO9914433 | 4/1998 | (WO) . |

*Primary Examiner*—Emily Bernhardt
(74) *Attorney, Agent, or Firm*—Peter C. Richardson; Paul H. Ginsburg; Roy F. Waldron

(57) ABSTRACT

A compound of the formula

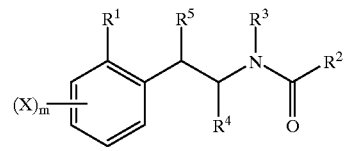

I wherein m, $R^1$, $R^2$, $R^3$, $R^4$, $R^5$ and X are as defined, useful in treating or preventing migraine, depression and other disorders for which a 5-$HT_1$ agonist or antagonist is indicated.

9 Claims, No Drawings

N-ACYL AND N-AROYL ARALKYLAMIDES

This application claims the benefit of the filing date of U.S. provisional patent application No. 60/081,970, filed Apr. 16, 1998.

BACKGROUND OF THE INVENTION

The present invention relates to novel N-acyl and N-aroyl aralkyl amides, to intermediates for their preparation, to pharmaceutical compositions containing them and to their medicinal use. The compounds of the present invention include selective agonists and antagonists of serotonin 1 (5-$HT_1$) receptors, specifically, of one or both of the 5-$HT_{1A}$ and 5-$HT_{1D}$ receptors. They are useful in treating or preventing migraine, depression and other disorders for which a 5-$HT_1$ agonist or antagonist is indicated.

European Patent Publication 434,561, published on Jun. 26, 1991, refers to 7-alkyl, alkoxy, and hydroxy substituted-1-(4-substituted-1-piperazinyl)-naphthalenes. The compounds are referred to as 5-$HT_1$ agonists and antagonists useful for the treatment of migraine, depression, anxiety, schizophrenia, stress and pain.

European Patent Publication 343,050, published on Nov. 23, 1989, refers to 7- unsubstituted, halogenated, and methoxy substituted-1-(4-substituted-1-piperazinyl)-naphthalenes as useful 5-$HT_{1A}$ ligand therapeutics.

PCT publication WO 94/21619, published Sep. 29, 1994, refers to naphthalene derivatives as 5-$HT_1$ agonists and antagonists.

PCT publication WO 96/00720, published Jan. 11, 1996, refers to naphthyl ethers as useful 5-$HT_1$ agonists and antagonists.

European Patent Publication 701,819, published Mar. 20, 1996, refers to the use of 5-$HT_1$ agonists and antagonists in combination with a 5-HT re-uptake inhibitor.

Glennon et al., refers to 7-methoxy-1-(1-piperazinyl)-naphthalene as a useful 5-$HT_1$ ligand in their article "5-$HT_{1D}$ Serotonin Receptors", *Clinical Drug Res. Dev.*, 22, 25–36 (1991).

Glennon's article "Serotonin Receptors: Clinical Implications", *Neuroscience and Behavioral Reviews*, 14, 35–47 (1990), refers to the pharmacological effects associated with serotonin receptors including appetite suppression, thermoregulation, cardiovascular/hypotensive effects, sleep, psychosis, anxiety, depression, nausea, emesis. Alzheimer's disease, Parkinson's disease and Huntington's disease.

World Patent Application WO 95/31988, published Nov. 30, 1995, refers to the use of a 5-$HT_{1D}$ antagonist in combination with a 5-$HT_{1A}$ antagonist to treat CNS disorders such as depression, generalized anxiety, panic disorder, agoraphobia, social phobias, obsessive-compulsive disorder, post-traumatic stress disorder, memory disorders, anorexia nervosa and bulimia nervosa, Parkinson's disease, tardive dyskinesias, endocrine disorders such as hyperprolactinaemia, vasospasm (particularly in the cerebral vasculature) and hypertension, disorders of the gastrointestinal tract where changes in motility and secretion are involved, as well as sexual dysfunction.

G. Maura al., *J. Neurochem*, 66 (1), 203–209 (1996), have stated that administration of agonists selective for 5-$HT_{1A}$ receptors or for both 5-$HT_{1A}$ and 5-$HT_{1D}$ receptors might represent a great improvement in the treatment of human cerebellar ataxias, a multifaceted syndrome for which no established therapy is available.

SUMMARY OF THE INVENTION

The present invention relates to a compound of the formula

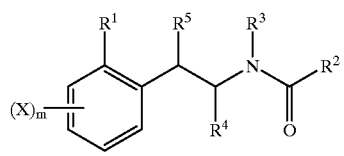

or the pharmaceutically acceptable salt thereof, wherein
$R^1$ is a group of the formua $G^1$, $G^2$, $G^3$, $G^4$, $G^5$ or $G^6$ depicted below:

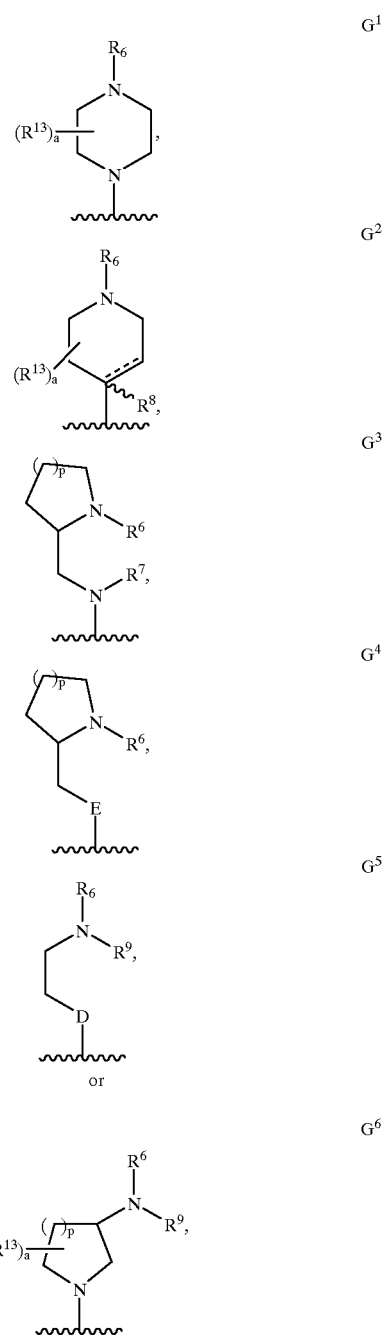

wherein the broken line indicates an optional double bond;
a is zero to eight;
m is 0, 1, 2, 3 or 4;

p is 1, 2 or 3;

D is oxygen, sulfur, SO, $SO_2$, or $NR^7$;

E is oxygen, sulfur, SO or $SO_2$;

X is hydrogen, chloro, fluoro, bromo, iodo, cyano, $(C_1-C_6)$alkyl, hydroxy, trifluoromethyl, $(C_1-C_6)$alkoxy, —$S(O)_t(C_1-C_6)$alkyl wherein t is 0, 1 or 2, —$CO_2R^{10}$ or —$CONR^{11}R^{12}$;

$R^2$ is —$(CH_2)_tB$, wherein t is 0, 1, 2 or 3, and B is hydrogen, phenyl, naphthyl or a 5 or 6 membered heteroaryl group containing from one to four heteroatoms in the ring, and wherein each of the foregoing phenyl, naphthyl and heteroaryl groups may optionally be substituted with one or more substituents independently selected from chloro, fluoro, bromo, iodo, $(C_1-C_6)$alkyl, $(C_1-C_6)$alkoxy, $(C_1-C_6)$alkoxy-$(C_1-C_6)$alkyl-, trifluoromethyl, trifluoromethoxy, cyano, hydroxy, —COOH and —$SO_n(C_1-C_6)$alkyl wherein n is 0, 1 or 2;

$R^3$ and $R^4$ are each independently hydrogen, $(C_1-C_4)$alkyl or —$(CH_2)_q$—J wherein q is 0, 1, 2 or 3, and J is phenyl or naphthyl, wherein said phenyl or naphthyl may be optionally substituted with one to three substituents independently selected from the group consisting of chloro, fluoro, bromo, iodo, $(C_1-C_6)$alkyl, $(C_1-C_6)$alkoxy, trifluoromethyl, cyano and —$S(O)_k(C_1-C_6)$alkyl wherein k is 0, 1 or 2;

$R^5$ is hydrogen or $(C_1-C_3)$alkyl;

$R^6$ is selected from the group consisting of hydrogen, $(C_1-C_6)$alkyl optionally substituted with $(C_1-C_6)$alkoxy or one to three fluorine atoms, or $[(C_1-C_4)$alkyl]aryl wherein the aryl moiety is phenyl, naphthyl, or heteroaryl-$(CH_2)_q$—, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and —$SO_g(C_1-C_6)$alkyl, wherein g is zero, one or two;

$R^7$ is selected from the group consisting of hydrogen, $(C_1-C_6)$alkyl, $[(C_1-C_4)$alkyl]aryl wherein the aryl moiety is phenyl, naphthyl, or heteroaryl-$(CH_2)_r$—, wherein the heteroaryl moiety is selected from the group consisting of pyridyl, pyrimidyl, benzoxazolyl, benzothiazolyl, benzisoxazolyl and benzisothiazolyl and r is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, —C(=O)—$(C_1-C_6)$alkyl, cyano and —$SO_j(C_1-C_6)$alkyl, wherein j is zero, one or two;

or $R^6$ and $R^7$ taken together form a 2 to 4 carbon chain;

$R^8$ is hydrogen or $(C_1-C_3)$alkyl;

$R^9$ is hydrogen or $(C_1-C_6)$alkyl;

or $R^6$ and $R^9$, together with the nitrogen atom to which they are attached, form a 5 to 7 membered heteroalkyl ring that may contain from zero to four heteroatoms selected from nitrogen, sulfur and oxygen;

each of $R^{10}$, $R^{11}$ and $R^{12}$ is selected, independently, from the radicals set forth in the definition of $R^3$, or $R^{11}$ and $R^{12}$, together with the nitrogen to which they are attached, form a 5 to 7 membered heteroalkyl ring that may contain from zero to four heteroatoms selected from nitrogen, sulfur and oxygen; and each $R^{13}$ is, independently, $(C_1-C_4)$alkyl or a $(C_1-C_4)$ methylene bridge from one of the ring carbons of the piperazine or piperidine ring of $G^1$ or $G^2$, respectively, to the same or another ring carbon or a ring nitrogen of the piperazine or piperidine ring of $G^1$ or $G^2$, respectively, having an available bonding site, or to a ring carbon of $R^6$ having an available bonding site;

with the proviso that when B is hydrogen, t is not zero; and with the proviso that when the broken line in formula $G^2$ is a double bond, $R^8$ is absent.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, ie, salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1 '-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds of this invention may contain olefin-like double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties. Unless otherwise indicated, halogen includes fluorine, chlorine. bromine, and iodine.

The term "a 5 or 6 membered heteroaryl group containing from one to four heteroatoms in the ring", as used herein, unless otherwise indicated, includes but is not limited to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indazolyl, isoquinolyl, quinolyl, phthalazinyl, quinoxalinyl, quinazolinyl or benzoxazinyl.

The term "a 5 to 7 membered heteroalkyl ring that may contain from one to four heteroatoms selected from nitrogen, sulfur and oxygen", as used herein, unless otherwise indicated, includes but is not limited to pyrrolidine, isoxazolidine, 1,3-oxazolidin-3-yl, isothiazolidine, 1,3-thiazolidin-3-yl, 1,2-pyrazolidin-2-yl, 1,3-pyrazolidin-1-yl, piperidine, thiomorpholine, 1,2-tetrahydrothiazin-2-yl, 1,3-tetrahydrothiazin-3-yl, tetrahydrothiadiazine, morpholine, 1,2-20 tetrahydrodiazin-2-yl, 1,3-tetrahydrodiazin-1-yl, piperazine.

Preferred compounds of the formula I include those wherein $R^1$ is

$R^6$ is $(C_1-C_6)$alkyl and $R^3$ is hydrogen.

Other preferred compounds of formula I include those wherein $R^2$ is phenyl or benzyl optionally substituted by chloro, fluoro, bromo, iodo, $(C_1-C_6)$alkyl or trifluoromethyl.

Other preferred compounds of formula I include those wherein $R^4$ is hydrogen or $(C_1-C_6)$alkyl.

More preferred compounds of formula I include those wherein $R^1$ is

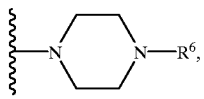

$R^6$ is $(C_1-C_6)$alkyl and $R^3$ is hydrogen, $R^2$ is phenyl or benzyl optionally substituted by chloro, fluoro, bromo, iodo, $(C_1-C_6)$alkyl or trifluoromethyl; and $R^4$ is hydrogen or $(C_1-C_6)$alkyl.

Specific preferred compounds of formula I include the following:
3,4-Dichloro-N-(2-[2-(4-methylpiperazin-1-yl)-phenyl]-ethyl)-benzamide;
4-Fluoro-N-(2-[2-(4-methylpiperazin-1-yl)-phenyl]-ethyl)-benzamide;
N-(2-[2-(4-methylpiperazin-1-yl)-phenyl]-ethyl)-benzamide;
3,4-Dichloro-N-(1-methyl-2-[2-(4-methylpiperazin-1-yl)-phenyl]-ethyl)-benzamide;
3,4-Dichloro-N-(1-methyl-2-[2-(4-methylpiperazin-1-yl)-phenyl]-propyl)-benzamide;
3,4-Dichloro-N-methyl-N-(2-[2-(4-methylpiperazin-1-yl)-phenyl]-ethyl)-benzamide;
N-Benzyl-N-(2-[2-(4-methylpiperazin-1-yl)-phenyl]-ethyl)-benzamide;
N-(4-chlorobenzyl)-N-2-[2-(4-methylpiperazin-1-yl)-phenyl]-ethyl)-benzamide;
3,4-Dichloro-N-(2-{2-[methyl-(1-methylpyrolidin-2-ylmethyl)-amino]-phenyl}-ethyl)-benzamide;
3,4-Dichloro-N-(2-{2-[(1-methyl-octahydro-pyrrolo[2,3-c]pyridin-6-yl)-phenyl]-ethyl}-benzamide;
3,4-Dichloro-N-{2-[2-(hexahydro-pyrrolo[1,2-a]pyrazin-2-yl)-phenyl]-ethyl}benzamide;
3,4-Dichloro-N-{2-[2-(1-methylpiperidin-4-yl)-phenyl]-ethyl)-benzamide;
3,4-Dichloro-N-{2-[2-(2-dimethylaminoethoxy)-phenyl]-ethyl}-benzamide;
3,4-Dichloro-N-{2-[2-(2-dimethylamino-ethylsulfanyl)-phenyl]-ethyl}-benzamide;
3,4-Dichloro-N-{2-[2-(2-pyrrolidin-1-ylethoxy)-phenyl]-ethyl}-benzamide;
4-Chloro-N-{2-[2-(3dimethylamino-pyrrolidin-1-yl)-phenyl]-ethyl}-benzamide:
4-Chloro-N-(2-{2-[methyl-(2-morpholin-4-yl-ethyl)-amino]-phenyl]-ethyl}-benzamide;
2-(4-Chlorophenyl)-N-{2-[2-(4-methylpiperazin-1-yl)-phenyl]-ethyl}-acetamide;
N-{2-[2-(4-Methylpiperazin-1-yl)-phenyl]-ethyl}-N-phenylacetamide;
N-{2-[2-(4-Methylpiperazin-1-yl)-phenyl]-ethyl}isonicotinamide;
N-{2-[2-(1-Azabicyclo[2.2.2]oct-4-yl)-phenyl]-ethyl}-N-methylbenzamide;
N-{2-[2-(1,4-Dimethylpiperidin-4-yl)-phenyl]-ethyl}-4-fluorobenzamide;
4-Fluoro-N-{2-[2-(9-methyl-3,9-diazabicyclo[3.3.1]non-3-yl)-phenyl]-ethyl}-benzamide;
N-(2-[2-(1,4-Diazabicyclo[3.3.1]non-4-yl)-phenyl]-ethyl}-N-methylbenzamide;
N-{1-Methyl-2-[2-(5-methyl-2,5-diazabicyclo[2.2.1]hept-2-yl)-phenyl]-ethyl}-benzamide;
2,4-Dichloro-N-methyl-N-{1-methyl-2-[2-(3-methyl-3,8-diazabicyclo[3.2.1]oct-8-yl)-phenyl]-ethyl}-benzamide;
N-{2-[2-(4-Methyl-octahydroquinoxalin-1-yl)-phenyl]-ethyl}-benzamide;
N-{2-[2-(1-Ethylpyrrolidin-2-ylmethoxy)-phenyl]-ethyl}-benzamide;
5-Phenyloxazole-2-carboxylic acid{2-[2-(4-methylpiperazin-1-yl)-phenyl]-ethyl}-amide;
5-Phenylthiophene-2-carboxylic acid{2-[2-(4-methylpiperazin-1-yl)-phenyl]-ethyl}-amide;
5-Methylthiophene-2-carboxylic acid{2-[2-(4-methylpiperazin-1-yl)-phenyl]-ethyl}-amide;
4-Fluoronaphthalene-1-carboxylic acid{2-[2-(4-methylpiperazin-1-yl)-phenyl]-ethyl}-amide;
5-Fluoro-1H-indole-2-carboxylic acid{2-[2-(4-methyl-piperazin-1-yl)-phenyl]-ethyl}-amide;
4-Chloro-N-{2-[2-(3,4,5-trimethylipiperazin-1-yl)-phenyl]-ethyl}-benzamide;
3,4-Dichloro-N-{2-[2-(2,4,5-trimethylpiperazin-1-yl)-phenyl]-ethyl}-benzamide; and
3,4-Dichloro-N-{2-[2-(2,4,6-trimethylpiperazin-1-yl)-phenyl]-ethyl}-benzamide.

The present invention also relates to a pharmaceutical composition for treating or preventing a disorder or condition selected from hypertension, depression, generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette syndrome, trichotillomania, kleptomania, male impotence, cancer (e.g. small cell lung carcinoma), chronic paroxysmal hemicrania and headache (associated with vascular disorders) in a mammal, preferably a human, comprising an amount of a compound of the formula I or a pharmaceutically acceptable salt thereof effective in treating or preventing such disorder or condition and a pharmaceutically acceptable carrier.

The present invention also relates to a pharmaceutical composition for treating or preventing a disorder or condition that can be treated or prevented by enhancing serotonergic neurotransmission in a mammal, preferably a human, comprising an amount of a compound of the formula I, or a pharmaceutically acceptable salt thereof, effective in treating or preventing such disorder or condition and a pharmaceutically acceptable carrier. Examples of such disorders and conditions are those enumerated in the preceding paragraph.

The present invention also relates to a method for treating or preventing a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (eg, agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette syndrome, trichotillomania, kleptomania, male impotence, cancer, (e.g., small cell lung carcinoma), chronic paroxysmal hemicrania and headache (associated with vascular disorders) in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a method for treating or preventing a disorder or condition that can be treated or prevented by enhancing serotonergic neurotransmission in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a pharmaceutical composition for treating or preventing a disorder or condition selected from hypertension, depression (e.g., depression in cancer patients, depression in Parkinson's patents, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence. Tourette syndrome, trichotillomania, kleptomania, male impotence, cancer (e.g., small cell lung carcinoma), chronic paroxysmal hemicrania and headache (associated with vascular disorders) in a mammal, preferably a human, comprising a serotonin receptor antagonizing or agonizing effective amount of a compound of the formula I, or a pharmaceutically acceptable salt thereof, and a pharmaceutically acceptable carrier.

The present invention also relates to a pharmaceutical composition for treating or preventing a disorder or condition that can be treated or prevented by enhancing serotonergic neurotransmission in a mammal, preferably a human, comprising a serotonin receptor antagonizing or agonizing effective amount of a compound of the formula I, or a pharmaceutically acceptable salt thereof, and a pharmaceutically acceptable carrier.

The present invention also relates to a method for treating or preventing a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette syndrome, trichotillomania, kleptomania, male impotence, cancer (e.g., small cell lung carcinoma), chronic paroxysmal hemicrania and headache (associated with vascular disorders) in a mammal, preferably a human, comprising administering to a mammal requiring such treatment or prevention a serotonin receptor antagonizing or agonizing effective amount of a compound of the formula I or a pharmaceutically acceptable salt thereof.

The present invention also relates to a method for treating or preventing a disorder or condition that can be treated or prevented by enhancing serotonergic neurotransmission in a mammal, preferably a human, comprising administering to a mammal requiring such treatment or prevention a serotonin receptor antagonizing or agonizing effective amount of a compound of the formula I or a pharmaceutically acceptable salt thereof.

The present invention relates to a pharmaceutical composition for treating or preventing a condition or disorder that can be treated or prevented by enhancing serotonergic neurotransmission in a mammal, preferably a human, comprising:

a) a pharmaceutically acceptable carrier;
b) a compound of the formula I or a pharmaceutically acceptable salt thereof, and
c) a 5-HT re-uptake inhibitor, preferably sertraline, or a pharmaceutically acceptable salt thereof;

wherein the amount of the active compounds (i.e., the compound of formula I and the 5-HT re-uptake inhibitor) are such that the combination is effective in treating or preventing such disorder or condition.

The present invention also relates to a method for treating or preventing a disorder or condition that can be treated or prevented by enhancing serotonergic neurotransmission in a mammal, preferably a human, comprising administering to a mammal requiring such treatment or prevention:

a) a compound of the formula I, defined above, or a pharmaceutically acceptable salt thereof; and
b) a 5-HT re-uptake inhibitor, preferably sertraline, or a pharmaceutically acceptable salt thereof, wherein the amounts of the active compounds (i.e., the compound of formula I and the 5-HT re-uptake inhibitor) are such that the combination is effective in treating or preventing such disorder or condition.

The present invention also relates to a method for treating or preventing a disorder or condition that can be treated or prevented by enhancing serotonergic neurotransmission in a mammal, preferably a human, comprising administering to said mammal requiring such treatment or prevention:

a) a 5-HT$_{1A}$ antagonist or a pharmaceutically acceptable salt thereof; and
b) a 5-HT$_{1D}$ antagonist of formula I or a pharmaceutically acceptable salt thereof;

wherein the amounts of each active compound (i.e., the 5-HT$_{1A}$ antagonist and the 5-HT$_{1D}$ antagonist) are such that the combination is effective in treating or preventing such disorder or condition.

The present invention also relates to a pharmaceutical composition for treating or preventing a disorder or condition that can be treated or prevented by enhancing serotonergic neurotransmission in a mammal, preferably a human, comprising:

a) a 5-HT$_{1A}$ antagonist or a pharmaceutically acceptable salt thereof, and
b) a 5-HT$_{1D}$ antagonist of formula I or a pharmaceutically acceptable salt thereof;

wherein the amounts of each active compound (i.e., the 5-HT$_{1A}$ antagonist and the 5-HT$_{1D}$ antagonist) are such that the combination is effective in treating or preventing such disorder or condition.

The present invention also relates to a compound of the formula

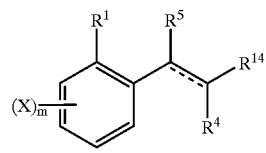

wherein the dashed line represents an optional double bond; $R^1$ is a group of the formua $G^1$, $G^2$, $G^3$, $G^4$, $G^5$ or $G^6$ depicted below:

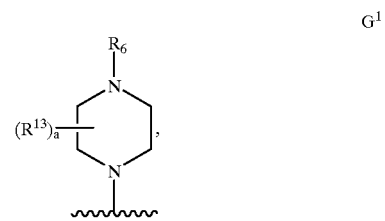

$G^1$

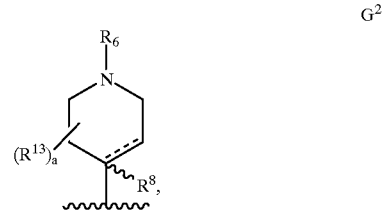

$G^2$

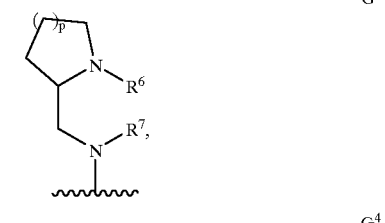

$G^3$

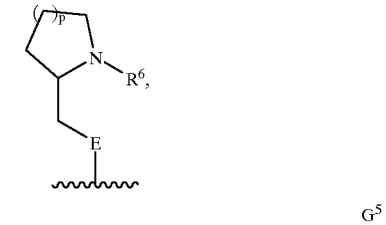

$G^4$

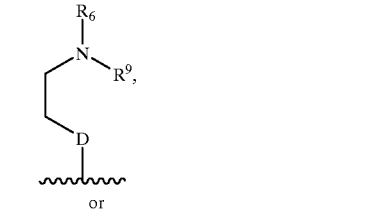

$G^5$ or

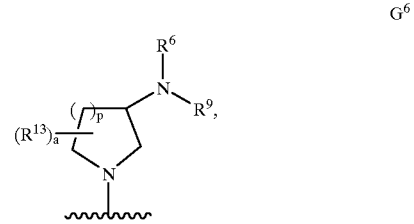

$G^6$ wherein the broken line indicates an optional double bond;

a is zero to eight;

m is 0, 1, 2, 3 or 4;

p is 1, 2 or 3;

D is oxygen, sulfur, SO, $SO_2$, or $NR^7$;

E is oxygen, sulfur, SO or $SO_2$;

X is hydrogen, chloro, fluoro, bromo, iodo, cyano $(C_1-C_6)$alkyl, hydroxy, trifluoromethyl, $(C_1-C_6)$alkoxy, $-S(O)_t(C_1-C_6)$alkyl wherein t is 0, 1 or 2, $-CO_2R^{10}$ or $-CONR^{11}R^{12}$;

$R^4$ is hydrogen, $(C_1-C_4$alkyl or $-(CH_2)_q-J$ wherein q is 0, 1, 2 or 3, and J is phenyl or naphthyl, wherein said phenyl or naphthyl may be optionally substituted with one to three substituents independently selected from the group consisting of chloro, fluoro, bromo, iodo, $(C_1-C_6)$alkyl, $(C_1-C_6)$alkoxy, trifluoromethyl, cyano and $-S(O)_k(C_1-C_6)$alkyl wherein k is 0, 1 or 2;

$R^5$ is hydrogen or $(C_1-C_3)$alkyl;

$R^6$ is selected from the group consisting of hydrogen, $(C_1-C_6)$alkyl optionally substituted with $(C_1-C_6)$alkoxy or one to three fluorine atoms, or $[(C_1-C_4)$alkyl]aryl wherein the aryl moiety is phenyl, naphthyl, or heteroaryl-$(CH_2)q$-, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and $-SO_g(C_1-C_6)$alkyl, wherein g is zero, one or two;

$R^7$ is selected from the group consisting of hydrogen, $(C_1-C_6)$alkyl, $[(C_1-C_4)$alkyl]aryl wherein the aryl moiety is phenyl, naphthyl, or heteroaryl-$(CH_2)_r$-, wherein the heteroaryl moiety is selected from the group consisting of pyridyl, pyrimidyl, benzoxazolyl, benzothiazolyl, benzisoxazolyl and benzisothiazolyl and r is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, $-C(=O)-(C_1-C_6)$alkyl, cyano and $-SO_j(C_1-C_6)$alkyl, wherein j is zero, one or two;

or $R^6$ and $R^7$ taken together form a 2 to 4 carbon chain;

$R^8$ is hydrogen or $(C_1-C_3)$alkyl;

$R^9$ is hydrogen or $(C_1-C_6)$alkyl;

or $R^6$ and $R^9$, together with the nitrogen atom to which they are attached, form a 5 to 7 membered heteroalkyl ring that may contain from zero to four heteroatoms selected from nitrogen, sulfur and oxygen;

each of $R^{10}$, $R^{11}$ and $R^{12}$ is selected, independently, from the radicals set forth in the definition of $R^3$; or $R^{11}$ and $R^{12}$, together with the nitrogen to which they are attached, form a 5 to 7 membered heteroalkyl ring that may contain from zero to four heteroatoms selected from nitrogen, sulfur and oxygen; and each $R^{13}$ is, independently, $(C_1-C_4)$alkyl or a $(C_1-C_4)$ methylene bridge from one of the ring carbons of the piperazine or piperidine ring of $G^1$ or $G^2$, respectively, to the same or another ring carbon or a ring nitrogen of the piperazine or piperidine ring of $G^1$ or $G^2$, respectively, having an available bonding site, or to a ring carbon of $R^6$ having an available bonding site;

$R^{14}$ is amino or nitro;

with the proviso that when $R^{14}$ is amino, the dashed line does not represent a double bond; and with the proviso that when the broken line in formula $G^2$ is a double bond, $R^8$ is absent.

"Enhanced serotonergic neurotransmission," as used herein, refers to increasing or improving the neuronal process whereby serotonin is released by a pre-synaptic cell upon excitation and crosses the synapse to stimulate or inhibit the post-synaptic cell.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbarbitol, and benzodiazepines (e.g., Valium (trademark)). "Treating a chemical dependency," as used herein, means reducing or alleviating such dependency.

Sertraline, (1S-cis)-4-(3,4-dichlorophenyl)-1,2,3,4-tetrahydro-N-methyl-1-naphthalenamine, as used herein has the chemical formula $C_{17}H_{17}NCl_2$ and the following structural formula

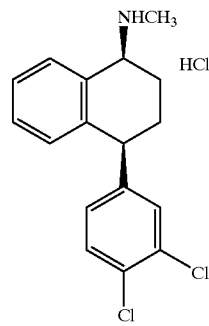

Its synthesis is described in U.S. Pat. 4,536,518, assigned to Pfizer Inc. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation.

DETAILED DESCRIPTION OF THE INVENTION

The following reaction Schemes illustrate the preparation of the compounds of the present invention. Unless otherwise indicated m, $R^1$, $R^2$, $R^3$, $R^4$, $R^5$ and X in the reaction Schemes and the discussion that follow are defined as above.

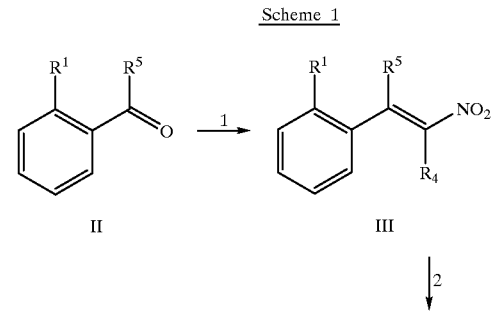

Scheme 1

-continued

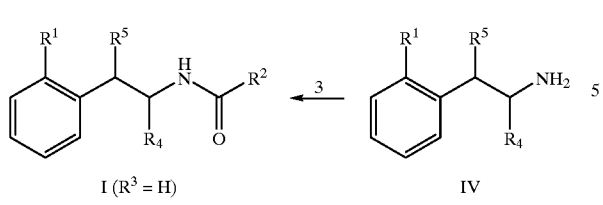

I (R³ = H)     IV

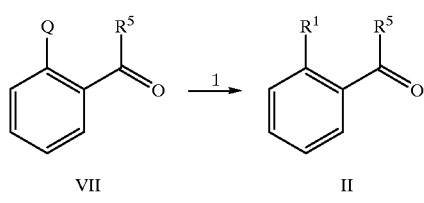

I (R³ not H)

Scheme 2

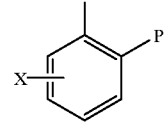

VII     II

Scheme 3

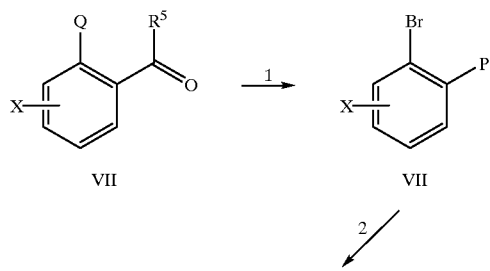

VII     VII

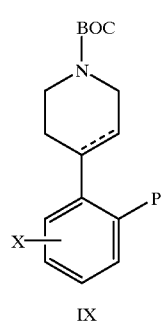

IX

-continued

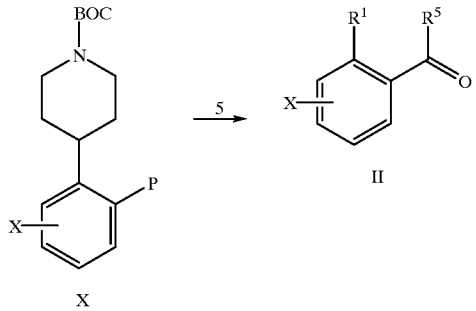

X     II

Scheme 4

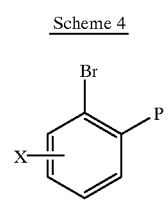

VIII

↓

XII

↓

XIII

Scheme 1 illustrates a method of synthesizing compounds of formula I wherein $R^1$ is a group of the formula $G^1$ though $G^6$ attached to an aromatic (e.g., phenyl) ring and $R^5$ is H or ($C_1$ to $C_3$) alkyl. Referring to Scheme 1, a compound of the formula II is reacted with a nitroalkyl compound of the formula $R^4CH_2NO_2$ in the presence of a base and in a organic solvent to generate nitroalkene of general formula III. Typically, the base employed is present as a salt, such as dimethylamine hydrochloride or ammonium acetate, as described by R. Royer in *Synthesis*, 1984, 12, 1054 or by H. Zhao et al in *J. Med. Chem.*, 1997, 40(8), 1186.

The intermediate nitroalkenes of formula III prepared as described above can then be converted to the alkylamines of general formula IV in one of two sequences. First, the carbon-carbon double bond of the nitroalkene may be selectively reduced in the presence of the nitro group through the use of specific reduction conditions. Such conditions can involve the use of selective reducing agents such as sodium borohydride or lithium borohydride at a temperature of about 0° C. to about 50° C. for a period of about 10 minutes to about 12 hours. Typically, the reduction is performed using methanol at 0° C. to 20° C., until the reaction is determined to be complete by thin-layer chromatography (tlc) or by instrumental techniques such as $^1$H-NMR or mass spectra. Representative conditions are described in *Synthetic Commun.*, 1985, 151.

The use of hydrogenation conditions (ref R. E. Harmon, et al *J. Org. Chem.*, 1969, 34, 3684) in the presence of a homogeneous catalyst such as chlorotris-(triphenylphosphine)rhodium(I) (i.e., Wilkinson's catalyst) has also been reported to selectively reduce the carbon-carbon double bond without reducing the nitro group.

The corresponding nitroalkyl intermediate thus prepared can subsequently be reduced to the compounds of general formula IV using reduction techniques familiar to one skilled in the art. For example, such intermediate nitroalkyl compounds can be reduced to the aminoalkyl compounds of formula IV using a metal, such as iron or zinc, in an acidic solvent such as acetic acid or aqueous hydrochloric acid at temperature of about 0° C. to about 50° C.

Alternatively, the intermediate of general formula III may be converted directly to the intermediate of general formula IV by the use of less selective agents which are capable of reducing the carbon-carbon double bond and the nitro group. Such reagents include metal hydrides, like lithium aluminum hydride (LAH) or sodium borohydride/borane, which have been used to perform similar conversions; LAH is preferred. Typical solvents for the reaction include ethers such as diethyl ether or THF and reaction temperatures from about 0° C. to about the boiling point of the solvent employed. Hydrogenation in the presence of a metal catalyst such as Pd or Pt, in an inert solvent such as methanol, ethanol or ethyl acetate at pressures of about one to about five atmospheres of hydrogen is also a method for this conversion.

The intermediates of general formula IV can then be converted to the amide compounds of general formula I (where $R^3$=H) by reacting the former with an acid anhydride of formula $(R^2CO)$—O— (COR $^{14}$), or an acid halide of formula $R^2CO$-A, wherein A is Cl, Br or I and $R^{14}$ is, for example, hydrogen or $R^2$. This conversion is well documented in the literature; for example, see Vogel, *Textbook of Practical Organic Chemistry*, 4th ed., Longman Group Ltd., London, 1978. This reaction is generally conducted in a reaction inert solvent, optionally in the presence of an acid scavenger such as triethylamine (TEA), pyridine, $Na_2CO_3$, $K_2CO_3$ and the like and at temperatures from about 0° C. to about the boiling point of the solvent employed in the amide formation.

Alternatively, the acid halide of formula $R^2COA$ may be reacted with the amino compound of formula IV under Schotten-Baumann conditions in the presence of a suitable base such as NaOH, in an aqueous medium and at a convenient temperature of about 0° C. to about 100° C., typically at room temperature, to prepare the amides of formula I (where $R^3$=H).

In another method, an acid of formula $R^2COOH$ and the amine of formula IV may be converted directly to the compounds of formula I (wherein $R^3$=H) by means of a dehydrating reagent such as dicyclohexylcarbodiimide (DCC), diphenylphosphoryl azide (DPA) or 1-(3-dimethylaminopropyl)-3-ethyl carbodiimide (DEC) in a suitable reaction inert solvent such as tetrahydrofuran (THF) or diethyl ether as described in *Tetrahedron Letters*, 1993, 34, 7685.

Finally, compounds of general formula I (where $R^3$=H) can be converted to compounds of general formula I (where $R^3 \neq$H) by alkylaton of the amide nitrogen using conditions and procedures well known to those skilled in the art of organic synthesis. For example, treatment of the compounds of formula I (where $R^3$=H) with a strong base such as sodium hydride, potassium hydride, sodium amide or lithium diisopropylamide (LDA) in a reaction inert solvent such as benzene, N,N-dimethylformamide (DMF) or N,N-dimethylacetamide (DMA), THF and the like, at temperatures from about −80° to about 100° C. are typically useful in generating an intermediate amide anion. Preferred conditions are sodium hydride and DMF at 25° C. The anion can then be reacted with an alkylating reagent of the formula $(R^3)_2SO_4$ or $R^3$-$L^1$, where $R^3$ is as previously defined and $L^1$ is a leaving group such as Cl, Br or I to produce the compound of general formula I.

Scheme 2 illustrates a method of synthesizing compounds of the formula II, the starting materials of Scheme 1, wherein $R^1$ is a group of the formula $G^1$, $G^3$, $G^4$, $G^5$ or $G^6$. Referring to Scheme 2, a compound of the formula VII, wherein Q is a suitable leaving group (e.g., chloro, fluoro, bromo, mesylate, tosylate, etc.), is reacted with a compound of the formula $R^1H$, wherein H refers to a hydrogen atom on group D or E or on nitrogen atoms from $G^1$, $G^3$, $G^5$ or $G^6$ and $R^1$ is a group of the formula $G^1$, $G^3$, $G^4$, $G^5$ or $G^6$ in the presence of a base, to form the corresponding compound of formula II. This reaction is generally carried out at a temperature from about 0° C. to about 140° C., preferably at about the reflux temperature, in a polar solvent such as dimethyl sulfoxide (DMSO), N,N-dimethylformamide (DMF), N,N-dimethylacetamide (DMA) or N-methyl-2-pyrrolidinone (NMP), preferably DMF. Suitable bases, when present, include anhydrous sodium carbonate ($Na_2CO_3$), potassium carbonate ($K_2CO_3$), sodium hydroxide (NaOH) and potassium hydroxide (KOH), as well as amines such as pyrrolidine, triethylamine and pyridine. Anhydrous potassium carbonate is preferred.

The starting materials of the formula VII are either commercially available or known in the art. For example, compounds of formula VII in which $R^5$ is hydrogen are readily available from commercial sources or may be prepared using procedures disclosed in the chemical literature. Compounds of the formula VII may also be prepared from the corresponding carboxylic acids or esters, (i.e., formula VII) wherein $R^5$=OH or O-alkyl), which are commercially available. These acids or esters can be reduced to the corresponding alcohols of formula XIV, depicted below, wherein Q is defined as for formula II, using one or more of a variety of reducing agents and conditions, depending upon the nature of the substituents Q and X.

XIV

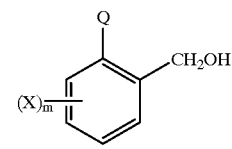

Such reducing agents include sodium borohydride ($NaBH_4$), sodium cyanoborohydride ($NaCNBH_3$), lithium aluminum hydride ($LiAlH_4$) and borane in THF ($BH_3$.THF) in solvents such as methanol, ethanol, THF, diethyl ether and dioxane. Oxidation of the alcohol of formula XIV to the corresponding aldehyde of formula VII (R$^5$=H) may be accomplished using a selective oxidizing agent such as Jones reagent (hydrogen chromate (H$_2$CrO$_4$)), pyridinium chlorochromate (PCC) or manganese dioxide (MnO$_2$). References for such conversions are readily available (e.g., K. B. Wiberg, *Oxidation in Organic Chemistry, Part A*, Academic Press Inc, N.Y., 69–72 (1965)).

The compounds of formula R$^1$H used in the preparation of intermediates of the formula VII are readily available or may be prepared using standard methods of organic synthesis known to those skilled in the art and adapted from procedures disclosed in the chemical literature. For example, the preparation of compounds of the formula R$^1$H, wherein R$^1$ is G$^1$, may be accomplished using the following reaction sequence, beginning with commercially available N-tert-butoxycarbonyl piperazine (XV):

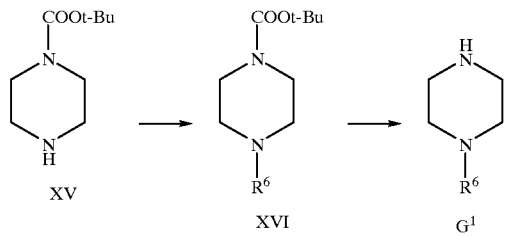

Alkylation of the compound of formula XV with a compound of the formula R$^6$L$^2$ wherein L$^2$ is a leaving group, and is defined as Q is defined above and R$^6$ is (C$_1$–C$_6$)alkyl, aryl-(C$_1$–C$_4$)alkyl wherein the aryl moiety is phenyl or naphthyl, or heteroaryl-(CH$_2$)q-, wherein q is zero, one, two, three or four, and the heteroaryl moiety is selected from pyridyl, pyrimidyl, benzoxazolyl, benzothiazolyl, benzisoxazolyl, and benzisothiazolyl, in the presence of an acid scavenger (e.g., sodium bicarbonate (NaHCO$_3$), potassium bicarbonate (KHCO$_3$), sodium carbonate (Na$_2$CO$_3$) or potassium carbonate (K$_2$CO$_3$)), in a polar solvent such as acetone at a temperature of about 10° C. to about the reflux temperature of the solvent, will yield the intermediate of formula XVI. Removal of the tert-butoxycarbonyl group can be accomplished using acidic conditions, e.g., HBr in acetic acid or trifluoroacetic acid until the reaction is judged to be complete.

Compounds of the formula II, wherein R$^1$ is tetrahydropyridine or piperidine (i.e. compounds of the formula G$^2$) and R$^2$ is hydrogen, can be prepared from the compounds of formula VII, many of which are commercially available, as depicted in Scheme 3. Referring to Scheme 3, the compound of formula VII is first converted into a protected aldehyde or ketone of the formula VIII, wherein P represents the entire protected aldehyde or ketone moiety, using methods well known in the art. For example, the 1,3-dioxolane derivative of the aldehyde may be prepared according to the method described by J. E. Cole et al., *J. Chem. Soc.*, 244 (1962), by refluxing a solution of the aldehyde of formula VII and 1,3-propanediol in anhydrous benzene with a catalytic amount of p-toluenesulfonic acid. When R$^5$ of formula VII is not hydrogen, the ketone can be protected using an appropriate protecting group. Appropriate protecting groups can be chosen from many such groups based on the presence and nature of the substituent X. Examples of suitable protecting groups may be found in T. W. Greene and P. Wuts, *Protecting Groups in Organic Synthesis*, John Wiley & Sons, 2nd Edition, New York, 1991. The most preferred protecting groups are those that are resistant to catalytic hydrogenation (e.g., 1, 3-dioxolane), which would therefore allow for the subsequent reduction, if required, of the carbon-carbon double bond of the tetrahydropyridines of formula IX.

Compounds of the formula VIII can then be treated with vinylstannanes of the formula

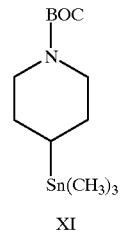

XI for example, 1-BOC4-trimethylstannyl-1,2,5,6-tetrahydropyridine (wherein BOC refers to tert-butyloxycarbonyl), in the presence of a catalyst, to form the corresponding compound of formula IX. Palladium is the preferred catalyst (for example, ((C$_6$H$_5$)$_3$P)$_4$Pd or Pd$_2$(dba)$_3$), wherein dba refers to dibenzylidene acetone. Suitable solvents for the reaction include neat, acetonitrile, dimethylformamide, N-methyl-2-pyrrolidinone, preferably dimethylformamide. This reaction is conveniently run at about 20° C. to about 160° C., preferably about 60° C. to about 130° C. This reaction may be carried out as described in "Palladium-catalyzed Vinylation of Organic Halides" in *Organic Reactions*, 2, 345–390, (W. G. Dauben, Ed., John Wiley & Sons, Inc., New York, N.Y., 1982).

Compounds of the formula IX can be converted into compounds of the formula II, wherein R$^1$ is tetrahydropyridine by removal of the aldehyde or ketone protecting group. The protecting group for the aldehyde or ketone, P, can be converted into the unprotected ketone or aldehyde of the formula —C(=O)R$^5$ using one or more of the techniques described in Greene, for example, stirring a solution of the compound of formula IX in THF and 5% hydrochloric acid at room temperature for 20 hours.

Alternatively, compounds of formula IX can be converted into compounds of the formula II, where R$^1$ is piperidine (G$^2$), by catalytic hydrogenation of the tetrahydropyridine of formula IX, from the previous paragraph, using standard methods known in the art, generally using palladium on carbon as the catalyst, to form the corresponding compounds of formula X. This reaction is typically performed in an inert solvent, such as ethanol or ethyl acetate, either with or without a protic acid such as acetic acid or hydrochloric acid (HCl). Acetic acid is preferred. The protecting groups on G$^2$ (e.g., BOC) can be removed using one or more of the techniques described in Greene, referred to above, for example, stirring the compound of formula X in ethyl acetate and 3 molar hydrochloric acid at about room temperature for about 30 minutes. The protecting group for the aldehyde or ketone, P, can be converted into the unprotected ketone or aldehyde II as described above.

Compounds of the formula VIII from reaction Scheme 3 may also be treated with alkyllithium reagents, for example n-butyllithium, sec-butyllithium or tert-butyllithium, preferably n-butyllithium in an inert solvent, as shown in Scheme 4, to form the intermediate lithium anion of formula XII. Suitable solvents for this reaction include, for example, ether or tetrahydrofuran, preferably tetrahydrofuran. Reaction temperatures can range from about −110° C. to about 0° C. The intermediate lithium anions of formula XII can then be further reacted with a suitable electrophile, selection of which depends on the presence and nature of the substituent X. Suitable electrophiles for use in preparing compounds of the formula II wherein $R^1$ is a group of the formula $G^2$ include, for example, carbonyl derivatives or alkylating agents (e.g., 1-BOC-4-piperidone). In the case where an aldehyde or ketone is used as the electrophile, the hydroxy group must be removed from the intermediate of formula XVIII, as depicted below, in order to form the corresponding compound of formula II.

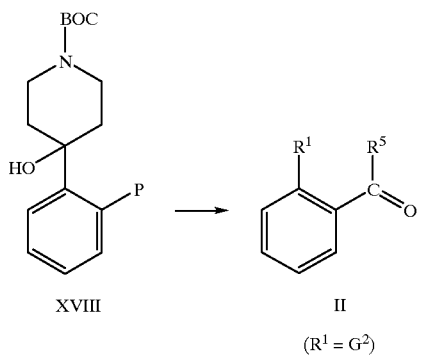

XVIII   II ($R^1 = G^2$)

This step may be accomplished by one of several standard methods known in the art. For example, a thiocarbonyl derivative such as a xanthate may be prepared and removed by free radical processes, both of which are known to those skilled in the art. Alternatively, the hydroxyl group may be removed by reduction with a hydride source such as triethysilane under acidic conditions, using, for example, trifluoroacetic acid or boron trifluoride. The reduction reaction can be performed neat or in a solvent such as methylene chloride. A further alternative would be to first convert the hydroxyl group to a suitable leaving group, such as tosylate or chloride, using standard methods known in the art, and then to remove the leaving group with a nucleophilic hydride, such as, for example, lithium aluminum hydride. The latter reaction is typically performed in an inert solvent such as ether or tetrahydrofuran. Also, a reducing agent may be used to reductively remove the benzylic substituent. Suitable reducing agents include, for example, Raney nickel in ethanol and sodium or lithium in liquid ammonia. Another alternative method for removing the hydroxyl group is to first dehydrate the alcohol of formula XVIII to an olefin of the formula IX (i.e. see Scheme 3) with a reagent such as Burgess salt (*J. Org. Chem.*, 38, 26 (1973)) and then to catalytically hydrogenate the double bond under standard conditions with a catalyst such as palladium on carbon. The alcohol may also be dehydrated to the olefin by treatment with acids such as p-toluenesulfonic acid.

Compounds of the formula If, wherein $R^1$ is $G^2$ and $R^6$ is hydrogen, can be converted into the corresponding compounds of the formula II, wherein $R^1$ is $G^2$ and $R^6$ is other than hydrogen, by reacting them with a compound of the formula $R^6L^2$, as described above for preparing compounds of the formula XVI.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^2$ includes a COOH or tetrazole moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are useful psychotherapeutics and are potent agonists and/or antagonists of the serotonin 1A (5-$HT_{1A}$) and/or serotonin 1D (5-$HT_{1D}$) receptors. The active compounds are useful in the treatment of hypertension, depression, generalized anxiety disorder, phobias (e.g., agoraphobia, social phobia and simple phobias), posttraumatic stress syndrome, avoidant personality disorder, sexual dysfunction (e, premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette syndrome, trichotillomania, kleptomania, male impotence, cancer (e.g., small cell lung carcinoma), chronic paroxysmal hemicrania and headache (associated with vascular disorders).

The affinities of the compounds of this invention for the various serotonin-1 receptors can be determined using standard radioligand binding assays as described in the literature. The 5-HT$_{1A}$ affinity can be measured using the procedure of Hoyer et al. (*Brain Res.*, 376, 85 (1986)). The 5-HT$_{1D}$ affinity can be measured using the procedure of Heuring and Peroutka (*J. Neurosci.*, 7, 894 (1987)).

The in vitro activity of the compounds of the present invention at the 5-HT$_{1D}$ binding site may be determined according to the following procedure. Bovine caudate tissue is homogenized and suspended in 20 volumes of a buffer containing 50 mM TRIS.hydrochloride (tris [hydroxymethyl]aminomethane hydrochloride) at a pH of 7.7. The homogenate is then centrifuged at 45,000 G for 10 minutes. The supernatant is then discarded and the resulting pellet resuspended in approximately 20 volumes of 50 mM TRIS.hydrochloride buffer at pH 7.7. This suspension is then pre-incubated for 15 minutes at 37° C., after which the suspension is centrifuged again at 45,000 G for 10 minutes and the supernatant discarded. The resulting pellet (approximately 1 gram) is resuspended in 150 ml of a buffer of 15 mM TRIS.hydrochloride containing 0.01 percent ascorbic acid with a final pH of 7.7 and also containing 10 $\mu$M pargyline and 4 mM calcium chloride (CaCl$_2$). The suspension is kept on ice at least 30 minutes prior to use.

The inhibitor, control or vehicle is then incubated according to the following procedure. To 50 $\mu$l of a 20 percent dimethylsulfoxide (DMSO)/80 percent distilled water solution is added 200 $\mu$l of tritiated 5-hydroxytryptamine (2 nM) in a buffer of 50 mM TRIS.hydrochloride containing 0.01 percent ascorbic acid at pH 7.7 and also containing 10 $\mu$M pargyline and 4 $\mu$M calcium chloride, plus 100 nM of 8-hydroxy-DPAT (dipropylaminotetraline) and 100 nM of mesulergine. To this mixture is added 750 $\mu$l of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GF/B-filters™). The pellet is then washed three times with 4 ml of a buffer of 50 mM TRIS.hydrochloride at pH 7.7. The pellet is then placed in a scintillation vial with 5 ml of scintillation fluid (aquasol 2 ™) and allowed to sit overnight. The percent inhibition can be calculated for each dose of the compound. An IC$_{50}$ value can then be calculated from the percent inhibition values.

The activity of the compounds of the present invention for 5-HT$_{1A}$ binding ability can be determined according to the following procedure. Rat brain cortex tissue is homogenized and divided into samples of 1 gram lots and diluted with 10 volumes of 0.32 M sucrose solution. The suspension is then centrifuged at 900 G for 10 minutes and the supernate separated and recentrifuged at 70,000 G for 15 minutes. The supernate is discarded and the pellet re-suspended in 10 volumes of 15 mM TRIS.hydrochloride at pH 7.5. The suspension is allowed to incubate for 15 minutes at 37° C. After pre-incubation is complete, the suspension is centrifuged at 70,000 G for 15 minutes and the supernate discarded. The resulting tissue pellet is resuspended in a buffer of 50 mM TRIS.hydrochloride at pH 7.7 containing 4 mM of calcium chloride and 0.01 percent ascorbic acid. The tissue is stored at −70° C. until ready for an experiment. The tissue can be thawed immediately prior to use, diluted with 10 $\mu$m pargyline and kept on ice.

The tissue is then incubated according to the following procedure. Fifty microliters of control, inhibitor, or vehicle (1 percent DMSO final concentration) is prepared at various dosages. To this solution is added 200 $\mu$l of tritiated 8-hydroxy DPAT at a concentration of 1.5 nM in a buffer of 50 mM TRIS.hydrochloride at pH 7.7 containing 4 mM calcium chloride, 0.01 percent ascorbic acid and pargyline. To this solution is then added 750 $\mu$l of tissue and the resulting suspension is vortexed to ensure homogeneity. The suspension is then incubated in a shaking water bath for 30 minutes at 37° C. The solution is then filtered, washed twice with 4 ml of 10 mM TRIS.hydrochloride at pH 7.5 containing 154 mM of sodium chloride. The percent inhibition is calculated for each dose of the compound, control or vehicle. IC$_{50}$ values are calculated from the percent inhibition values.

The compounds of formula I of the present invention described in the following Examples were assayed for 5-HT$_{1A}$ and 5-HT$_{1D}$ affinity using the aforementioned procedures. All such compounds of the invention that were tested exhibited IC$_{50}$'s less than 0.60 $\mu$M for 5-HT$_{1D}$ affinity and IC$_{50}$'s less than 1.0 $\mu$M for 5-HT$_{1A}$ affinity.

The agonist and antagonist activities of the compounds of the invention at 5-HT$_{1A}$ and 5-HT$_{1D}$ receptors can be determined using a single saturating concentration according to the following procedure. Male Hartley guinea pigs are decapitated and 5-HT$_{1A}$ receptors are dissected out of the hippocampus, while 5-HT$_{1D}$ receptors are obtained by slicing at 350 mm on a McIlwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000×g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contains 2.0 mM MgCl$_2$, 0.5 mM ATP, 1.0 mM cAMP, 0.5 mM IBMX, 10 mM phosphocreatine, 0.31 mg/mL creatine phosphokinase, 100 $\mu$M GTP and 0.5–1 microcuries of [$^{32}$P]-ATP (30 Ci/mmol: NEG-003—New England Nuclear). Incubation is initiated by the addition of tissue to siliconized microfuge tubes (in triplicate) at 30° C. for 15 minutes. Each tube receives 20 $\mu$L tissue, 10 $\mu$L drug or buffer (at 10X final concentration), 10 $\mu$L 32 nM agonist or buffer (at 10X final concentration), 20 $\mu$L forskolin (3 $\mu$M final concentration) and 40 $\mu$L of the preceding reaction mix. Incubation is terminated by the addition of 100 $\mu$L 2% SDS, 1.3 mM cAMP, 45 mM ATP solution containing 40,000 dpm [$^3$H]-cAMP (30 Ci/mmol: NET-275 - New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 5, 541–548. Radioactivity is quantified by liquid scintillation counting. Maximal inhibition is defined by 10 $\mu$M (R)-8-OH-DPAT for 5-HT$_{1A}$ receptors, and 320 nM 5-HT for 5-HT$_{1D}$ receptors. Percent inhibitions by the test compounds are then calculated in relation to the inhibitory effect of (R)-8-OH-DPAT for 5-HT$_{1A}$ receptors or 5-HT for 5-HT$_{1D}$ receptors. The reversal of agonist induced inhibition of forskolin-stimulated adenylate cyclase activity is calculated in relation to the 32 nM agonist effect.

The compounds of the invention can be tested for in vivo activity for antagonism of 5-HT$_{1D}$ agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneously (s.c.) prior to a 5-HT$_{1D}$ agonist, such as [3-(1-methylpyrrolidin-2-ylmethyl)-1H-indol-5-yl]-(3-nitropyridin-3-yl)-amine, which can be prepared as described in PCT publication WO93/111 06, published Jun. 10, 1993 and which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-HT$_{1D}$ agonist is then administered at 0 minutes and temperatures are taken 30, 60, 120 and 240 minutes later.

In subcutaneous screening experiments, a pre-drug baseline temperature reading is made at −30 minutes. The test compound and 5-HT$_{1D}$ agonists are given concurrently and temperatures are taken at 30, 60, 120 and 240 minutes later.

Data are analyzed with two-way analysis of variants with repeated measures in Newman-Keuls post hoc analysis.

The active compounds of the invention can be evaluated as anti-migraine agents by testing the extent to which they mimic sumatriptan in contracting the dog isolated saphenous vein strip [P. P. A. Humphrey et al., *Br. J. Pharmacol.*, 94, 1128 (1988)]. This effect can be blocked by methiothepin, a known serotonin antagonist. Sumatriptan is known to be useful in the treatment of migraine and produces a selective increase in carotid vascular resistance in the anesthetized dog. The pharmacological basis of sumatriptan efficacy has been discussed in W. Fenwick et al., *Br. J. Pharmacol.*, 96, 83 (1989).

The serotonin 5-HT$_1$ agonist activity can be determined by the in vitro receptor binding assays, as described for the 5-HT$_{1A}$ receptor using rat cortex as the receptor source and [$^3$H]-8-OH-DPAT as the radioligand [D. Hoyer et al. *Eur. J. Pharm.*, 118, 13 (1985)] and as described for the 5-HT$_{1D}$ receptor using bovine caudate as the receptor source and [$^3$H]serotonin as the radioligand [R. E. Heuring and S. J. Peroutka, *J. Neuroscience*, 7, 894 (1987)]. Of the active compounds tested, all exhibited an IC$_{50}$ in either assay of 1 μM or less.

The compounds of formula I may advantageously be used in conjunction with one or more other therapeutic agents, for instance, different antidepressant agents, such as tricyclic antidepressants (e.g., amitriptyline, dothiepin, doxepin, trimipramine, butripyline, clomipramine, desipramine, imipramine, iprindole, lofepramine, nortriptyline or protriptyline), monoamine oxidase inhibitors (e.g., isocarboxazid, phenelzine or tranylcyclopramine) or 5-HT re-uptake inhibitors (e.g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist e.g., bromocriptine, lysuride or pergolide). It is to be understood that the present invention covers the use of a compound of general formula (I) or a physiologically acceptable salt or solvate thereof in combination with one or more other therapeutic agents.

Compounds of the formula I and the pharmaceutically acceptable salts thereof, in combination with a 5-HT re-uptake inhibitor (e.g., fluvoxamine, sertraline, fluoxetine or paroxetine), preferably sertraline, or a pharmaceutically acceptable salt or polymorph thereof (the combination of a compound of formula I with a 5-HT re-uptake inhibitor is referred herein to as "the active combination"), are useful psychotherapeutics and may be used in the treatment or prevention of disorders the treatment or prevention of which is facilitated by enhanced serotonergic neurotransmission (e.g., hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders (e.g., dementia, amnestic disorders, and age-associated memory impairment), Parkinson's diseases (e.g., dementia in Parkinson3 s disease, neuroleptic-induced Parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion) chronic paroxysmal hemicrania and headache (associated with vascular disorders).

Serotonin (5-HT) re-uptake inhibitors, preferably sertraline, exhibit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

U.S. Pat. No. 4,536,518 describes the synthesis, pharmaceutical composition and use of sertraline for depression and is hereby incorporated by reference in its entirety.

Activity of the active combination as antidepressants and related pharmacological properties can be determined by methods (1)–(4) below, which are described in Koe, B. et al., *Journal of Pharmacology and Experimental Therapeutics*, 226 (3), 686–700 (1983). Specifically, activity can be determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No. 4,029,731.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., depression) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 $\mu$g to 1000 $\mu$g of the compound of the invention. The overall daily dose with an aerosol will be within the range 100 $\mu$g to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in.amounts which are sufficient to provide the desired unit dosage.

A proposed daily dose of an active compound of this invention in the combination formulation (a formulation containing an active compound of this invention and a 5HT re-uptake inhibitor) for oral, parenteral, rectal or, buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 $\mu$g to about 100 mg of the active compound of this invention, preferably from about 1

μg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a 5-HT re-uptake inhibitor, preferably sertraline, preferably from about 1 mg to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg to about 100 mg per kg of body weight per day of a 5-HT re-uptake inhibitor, preferably sertraline, preferably from about 0.1 mg. to about 10 mg per kg of body weight per day of sertraline; with from about 0.001 mg. to about 100 mg per kg of body weight per day of a compound of formula I, preferably from about 0.01 mg to about 10 mg per kg of body weight per day of a compound of formula I, although variations will necessarily occur depending upon the conditions of the subject being treated and the particular route of administration chosen.

The following Examples illustrate the preparation of the compounds of the present invention. Melting points are uncorrected. NMR data are reported in parts per million ($\delta$) and are referenced to the deuterium lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63 μm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

Preparation 1

2-[2-(4-methylpiperazin-1yl)phenyl]-ethylamine

A mixture of 2-(4-methylpiperazin-1-yl)benzaldehyde (5 grams, 24.5 mmol, prepared according to the method of D. Reinhoudt et al., Synthesis, 1987, 641), dimethylamine hydrochoride (4 grams, 49 mmol), potassium fluoride (0.213 grams, 3.7 mmol) and nitromethane (100 mL) in anhydrous toluene (100 mL) was refluxed under nitrogen using a Dean Stark trap to collect the azeotroped water. After 2 hour the reaction was determined to be completed by thin layer chromatography using triethylamine: methanol: ethyl acetate (5:10:85). The solvents were removed in vacuo and the residue was partitioned between methylene chloride and saturated aqueous sodium carbonate. The organic layer was then washed with saturated sodium chloride, dried and concentrated to a red oil, 5.69 grams. Chromatography using silica gel on a 4×1.75 inch column, eluting with 100% ethyl acetate followed by increasing percentages of methanol, produced 4.03 grams of 1-methyl-4-[2-(2-nitrovinyl)-phenyl]-piperazine as a light orange solid.

$^1$H-nmr (CDCl$_3$, 400 MHz) $\delta$8.35 (1H, d, J=13.9 Hz), 7.66 (1H, d, J=13.7 Hz), 7.46 (2H, m), 7.10 (2H, m), 2.99 (4H, m), 2.63 (4H, m), 2.38 (3H, s).

A slurry of sodium borohydride (0.395 grams, 10.43 mmol) in 30 mL tetrahydrofuran and 30 mL methanol, cooled to 0° C., was treated with 2.57 grams (10.43 mmol) of the preceding compound and allowed to stir at room temperature for 60 hours. The solvents were removed in vacuo, the residue was partitioned between methylene chloride and water, the organic layer was washed with saturated aqueous sodium chloride, dried and concentrated to a brown foam, 2.06 grams. Flash chromatography on 4.3 grams of silica gel, eluting with 300 mL of methanol: ethyl acetate (1:99) followed by 400 mL of triethylamine: methanol: ethyl acetate (1:3:96) produced 0.355 grams of 1-methyl-4-[2-(2-nitroethyl)-phenyl]-piperazine as a yellow oil which slowly solidified. $^1$H-nmr (CDCl$_3$, 400 MHz) $\delta$7.07–7.27 (4H, m), 4.67 (2H, t), 3.34 (2H, t), 2.90 (4H, m) 2.57 (4H, m), 2.35 (3H, s). Mass spectrum: 250 (m$^{+1}$).

A mixture of the above nitroethyl intermediate (0.200 grams, 0.803 mmol) and iron filings (0.900 grams, 16 mmol) in 5.0 mL of acetic acid was refluxed for 1.5 hours. After cooling to room temperature, the mixture was evaported in vacuo and the residue was partitioned between methylene chloride and 1 N sodium hydroxide. The organic layer was separated and washed several times with saturated aqueous sodium chloride, dried and concentrated in vacuo to produce 2-[2-(4-methylpiperazin-1-yl)phenyl]-ethylamine as a tan oil, 0.108 grams. Mass spectrum: 220 (m$^{+1}$).

Preparation 2

2-[2-(4-methylpiperazin-1-yl)phenyl]-ethylamine

Under nitrogen in a 200 mL flask, lithium aluminum hydride (1.6 g, 42.2 mmol) was added portionwise to 60 mL of anhydrous diethyl ether. To this was added a solution of 1-methyl-4[2-nitrovinyl)-phenyl]-piperazine (3.7 grams, 15 mmol), prepared according to Preparation 1, in 40 mL of tetrahydrofuran (THF) over a 30 minute period so as to control the vigorous evolution of hydrogen gas. The resulting light tan suspension was stirred for 36 hours at room temperature. The reaction was worked up by cautiously adding 2 mL of water, 4 mL of 15% aqueous sodium hydroxide, 6 mL of water and stirring for an additional 1 hour. The mixture was filtered through d.e. and concentrated to give the title product as a dark amber colored oil, 3.01 grams. $^1$H-nmr (DMSO-d$_6$, 300 MHz) d 7.20–6.97 (m, 4H), 2.82–2.77 (m, 7H), 2.72–2.67 (m, 2H), 2.47 (br m, 5H), 2.23 (s, 3H). $^{13}$C-nmr (DMSO-d$_6$ 300 MHz) 151.6, 135.3, 129.7, 126.7, 123.6, 119.9, 55.3, 52.3, 45.9, 42.8, 34.8 ppm. Mass spectrum: 220 (m$^{+1}$, 75%), 203 (m$^{+1}$-NH3, 100%).

EXAMPLE 1

3,4-dichloro-N-(2-[2-(4-methylpiperazin-1-yl) phenyl]-ethyl)-benzamide hydrochloride monohydrate A mixture of 2-[2-(4-methylpiperazin-1-yl)phenyl]-ethylamine (0.107 grams, 0.49 mmol) and triethylamine (TEA, 88 mL, 0.64 mmol) in 6 mL of anhydrous tetrahydrofuran (THF) was treated with 3,4-dichlorobenzoyl chloride (0.113 grams, 0.53 mmol) and stirred overnight at room temperature. A thin-layer chromatography (tlc, silica gel) eluted with triethylamine: methanol: ethyl acetate (5:10:85) indicated a new product formed with Rf of approximately 0.5. The solvent was removed under vacuum on a rotary evaporator and the residue was partitioned between methylene chloride and saturated aqueous sodium carbonate, the organic layer was washed with saturated sodium chloride, dried over magnesium sulfate and concentrated in vacuo to a brown foam, 0.175 grams. The foam was absorbed onto silica gel and flash chromatographed, eluting with ethyl acetate:hexanes (50:50) followed by increasing percentages of ethyl acetate and triethylamine to obtain the crude product as a tan foam, 0.94 mg. This was converted to the hydrochloride salt using 4.0 molar hydrochloric acid in 1,4-dioxane. Recrystallization from isopropanol produced a light tan solid, m.p. 110–120° C. $^1$H-nmr (400 MHz, d$_6$-DMSO) δ10.45 (1H, br s), 8.94 (1H, t, J=5 Hz), 8.07 (1H, t, J=2 Hz), 7.83 (1H, t, J=2 Hz), 7.81 (1H, t, J=2 Hz), 7.74 (1H, d, J=2.1 Hz), 3.53–3.40 (2H, m), 3.19–3.00 (4H, m), 2.90–2.80 (5H, m). Mass spectrum (APCl): 392 (m$^{+1}$). Elemental analysis calculated for $C_{20}H_{23}N_3OCl_2·HCl·H_2O$: C, 53.76; H, 5.87 N, 9.40. Found: C, 54.05; H, 5.62; N, 9.26.

The title compounds of examples 2–4 were prepared by method analogous to that described in Example 1.

EXAMPLE 2

Thiophene-2-carboxylic acid {2-[2-(4-methylpiperazin-1-yl)-phenyl]ethyl}amide hydrochloride hydrate Melting point 236–238° C. Mass spectrum (APCl$^+$): 330 (m$^{+1}$, 100%). Elemental analysis calculated for $C_{18}H_{23}N_3OS·HCl·0.25\ H_2O$: C, 58.36, H, 6.67, N 11.34. Found: C, 58.57, H, 6.72, N, 11.24.

EXAMPLE 3

4-methoxy-N-{2-[2-(4-methylpiperazin-1-yl)-phenyl]ethyl}-benzamide Mass spectrum (APCl+): 338 (m$^{+1}$).

EXAMPLE 4

2,6-difluoro-N-{2-[2-(4-methylpiperazin-1-yl)-phenyl]ethyl}-benzamide Mass spectrum (APCl+): 360 (m$^{+1}$).

What is claimed is:

1. A compound of the formula

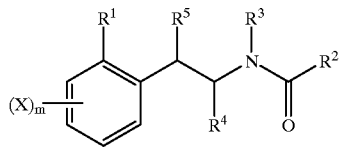

or the pharmaceutically acceptable salt thereof, wherein $R^1$ is a group of the formula $G^1$ or $G^5$ depicted below:

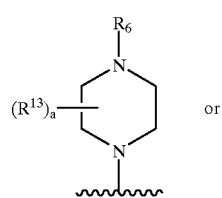

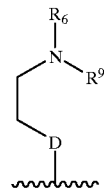

a is zero to eight;
m is 0, 1, 2, 3 or 4;
D is $NR^7$;
X is hydrogen, chloro, fluoro, bromo, iodo, cyano, ($C_1$–$C_6$)alkyl, hydroxy, trifluoromethyl, ($C_1$–$C_6$)alkoxy, —S(O)$_t$($C_1$–$C_6$)alkyl wherein t is 0, 1 or 2, —CO$_2$R$^{10}$ or —CONR$^{11}$R$^{12}$;
$R^2$ is —(CH$_2$)$_t$B, wherein t is 0, 1, 2 or 3, and B is hydrogen, phenyl, naphthyl, pyridinyl, oxazolyl, indolyl, or thienyl, and wherein each of the foregoing phenyl, naphthyl, pyridinyl, oxazolyl, indolyl, and thienyl groups may optionally be substituted with one or more substituents independently selected from chloro, fluoro, bromo, iodo, ($C_1$–$C_6$)alkyl, ($C_1$–$C_6$)alkoxy, ($C_1$–$C_6$)alkoxy-($C_1$–$C_6$)alkyl-, trifluoromethyl, trifluoromethoxy, cyano, hydroxy, —COOH and —SO$_n$($C_1$–$C_6$)alkyl wherein n is 0, 1 or 2;
$R^3$ and $R^4$ are each independently hydrogen, ($C_1$–$C_4$)alkyl or —(CH$_2$)$_q$-J wherein q is 0, 1, 2 or 3, and J is phenyl or naphthyl, wherein said phenyl or naphthyl may be optionally substituted with one to three substituents independently selected from the group consisting of chloro, fluoro, bromo, iodo, ($C_1$–$C_6$)alkyl, ($C_1$–$C_6$)alkoxy, trifluoromethyl, cyano and —S(O)$_k$($C_1$–$C_6$)alkyl wherein k is 0, 1 or 2;
$R^5$ is hydrogen or ($C_1$–$C_3$)alkyl;
$R^6$ is selected from the group consisting of hydrogen, ($C_1$–$C_6$)alkyl optionally substituted with ($C_1$–$C_6$)alkoxy or one to three fluorine atoms, or —($C_1$–$C_4$)alkylaryl wherein the aryl moiety is phenyl or naphthyl, and wherein said aryl moiety may optionally be substituted with one or more substituents independently selected from the group consisting of chloro, fluoro, bromo, iodo, ($C_1$–$C_6$)alkyl, ($C_1$–$C_6$)alkoxy, trifluoromethyl, cyano and —SO$_g$($C_1$–$C_6$)alkyl, wherein g is zero, one or two;
or if $R^1$ is $G^5$, $R^6$ and $R^7$ taken together form a 2 carbon chain;
$R^9$ is hydrogen or ($C_1$–$C_6$)alkyl;
each of $R^{10}$, $R^{11}$ and $R^{12}$ is selected, independently, from the radicals set forth in the definition of $R^3$; and
each $R^{13}$ is ($C_1$–$C_4$)alkyl;
with the proviso that when B is hydrogen, t is not zero.

2. A compound according to claim 1, wherein $R^1$ is

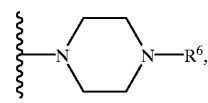

$R^6$ is ($C_1$–$C_6$)alkyl and $R^3$ is hydrogen.

3. A compound according to claim 1, wherein $R^2$ is phenyl or benzyl optionally substituted by chloro, fluoro, bromo, iodo, ($C_1$–$C_6$)alkyl or trifluoromethyl.

4. A compound according to claim 1, wherein $R^4$ is hydrogen or $(C_1-C_6)$alkyl.

5. A compound according to claim 1, wherein $R^1$ is

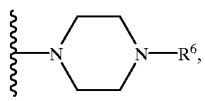

$R^6$ is $(C_1-C_6)$alkyl and $R^3$ is hydrogen; $R^2$ is phenyl or benzyl optionally substituted by chloro, fluoro, bromo, iodo, $(C_1-C_6)$alkyl or trifluoromethyl; and $R^4$ is hydrogen or $(C_1-C_6)$alkyl.

6. A compound according to claim 1, wherein said compound is selected from the group consisting of:

3,4-Dichloro-N-(2-[2-(4-methylpiperazin-1-yl)-phenyl]-ethyl)-benzamide;
4-Fluoro-N-(2-[2-(4-methylpiperazin-1-yl)-phenyl]-ethyl)-benzamide;
N-(2-[2-(4-methylpiperazin-1-yl)-phenyl]-ethyl)-benzamide;
3,4-Dichloro-N-(1-methyl-2-[2-(4-methylpiperazin-1-yl)-phenyl]-ethyl)-benzamide;
3,4-Dichloro-N-(1-methyl-2-[2-(4-methylpiperazin-1-yl)-phenyl]-propyl)-benzamide;
3,4-Dichloro-N-methyl-N-(2-[2-(4-methylpiperazin-1-yl)-phenyl]-ethyl)-benzamide;
N-Benzyl-N-(2-[2-(4-methylpiperazin-1-yl)-phenyl]-ethyl)-benzamide;
N-(4-chlorobenzyl)-N-(2-[2-(4-methylpiperazin-1-yl)-phenyl]-ethyl)-benzamide;
2-(4-Chloro-phenyl)-N-{2-[2-(4-methylpiperazin-1-yl)-phenyl]-ethyl}-acetamide;
N-{2-[2-(4-Methylpiperazin-1-yl)-phenyl]-ethyl}-N-phenylacetamide;
N-{2-[2-(4-Methylpiperazin-1-yl)-phenyl]-ethyl}-isonicotinamide;
5-Methylthiophene-2-carboxylic acid {2-[2-(4-methylpiperazin-1-yl)-phenyl]-ethyl}-amide;
4-Fluoronaphthalene-1-carboxylic acid {2-[2-(4-methylpiperazin-1-yl)-phenyl]-ethyl}-amide;
5-Fluoro-1H-indole-2-carboxylic acid{2-[2-(4-methylpiperazin-1-yl)-phenyl]-ethyl}-amide;
4-Chloro-N-{2-[2-(3,4,5-trimethylpiperazin-1-yl)-phenyl]-ethyl}-benzamide;
3,4-Dichloro-N-{2-[2-(2,4,5-trimethylpiperazin-1-yl)-phenyl]-ethyl}-benzamide;
3,4-Dichloro-N-{2-[2-(2,4,6-trimethylpiperazin-1-yl)-phenyl]-ethyl}-benzamide; and pharmaceutically acceptable salts thereof.

7. A compound according to claim 1, wherein said compound is selected from the group consisting of:

3,4-dichloro-N-(2-[2-(4-methylpiperazin-1-yl)phenyl]-ethyl)-benzamide;
thiophene-2-carboxylic acid {2-[2-(4-methylpiperazin-1-yl)-phenyl]ethyl}amide;
4-methoxy-N-{2-[2-(4-methylpiperazin-1-yl)-phenyl]ethyl}-benzamide;
2,6-difluoro-N-{2-[2-(4-methylpiperazin-1-yl)-phenyl]ethyl]-benzamide; and pharmaceutically acceptable salts thereof.

8. A compound of the formula

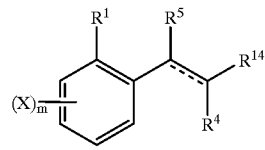

wherein the dashed line represents an optional double bond;
$R^1$ is a group of the formula $G^1$ or $G^5$ depicted below:

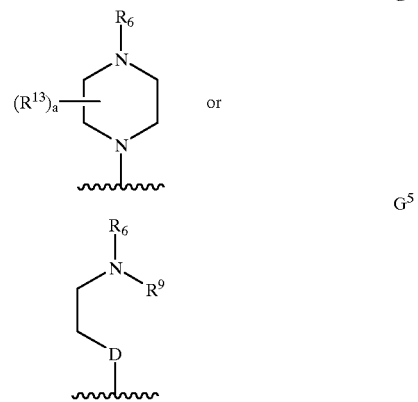

a is zero to eight;
m is 0, 1, 2, 3 or 4;
D is $NR^7$;
X is hydrogen, chloro, fluoro, bromo, iodo, cyano, $(C_1-C_6)$alkyl, hydroxy, trifluoromethyl, $(C_1-C_6)$alkoxy, —S(O)$_t$($C_1-C_6$)alkyl wherein t is 0, 1 or 2, —CO$_2$R$^{10}$ or —CONR$^{11}$R$^{12}$;
$R^4$ is hydrogen, $(C_1-C_4)$alkyl or —(CH$_2$)$_q$-J wherein q is 0, 1, 2 or 3, and J is phenyl or naphthyl, wherein said phenyl or naphthyl may be optionally substituted with one to three substituents independently selected from the group consisting of chloro, fluoro, bromo, iodo, $(C_1-C_6)$alkyl, $(C_1-C_6)$alkoxy, trifluoromethyl, cyano and —S(O)$_k$($C_1-C_6$)alkyl wherein k is 0, 1 or 2;
$R^5$ is hydrogen or $(C_1-C_3)$alkyl;
$R^6$ is selected from the group consisting of hydrogen, $(C_1-C_6)$alkyl optionally substituted with $(C_1-C_6)$alkoxy or one to three fluorine atoms, or —($C_1-C_4$)alkylaryl wherein the aryl moiety is phenyl or naphthyl, and wherein said aryl moiety may optionally be substituted with one or more substituents independently selected from the group consisting of chloro, fluoro, bromo, iodo, $(C_1-C_6)$alkyl, $(C_1-C_6)$alkoxy, trifluoromethyl, cyano and —SO$_g$($C_1-C_6$)alkyl, wherein g is zero, one or two;
or if $R^1$ is $G^5$, $R^6$ and $R^7$ taken together form a 2 carbon chain;
$R^9$ is hydrogen or $(C_1-C_6)$alkyl;
each of $R^{10}$, $R^{11}$ and $R^{12}$ is selected, independently, from the radicals set forth in the definition of $R^3$; and
each $R^{13}$ is $(C_1-C_4)$alkyl;
$R^{14}$ is amino or nitro;
with the proviso that when $R^{14}$ is amino, the dashed line does not represent a double bond.

9. A pharmaceutical composition comprising an amount of a compound according to claim 1 and a pharmaceutically acceptable carrier.

* * * * *